US012042505B2

(12) United States Patent
Driscoll

(10) Patent No.: US 12,042,505 B2
(45) Date of Patent: Jul. 23, 2024

(54) COMPOSITIONS AND METHODS FOR TREATING DRY EYE

(71) Applicant: Diana Driscoll, Keller, TX (US)

(72) Inventor: Diana Driscoll, Keller, TX (US)

(73) Assignee: GENETIC DISEASE INVESTIGATORS, LLC, Keller, TX (US)

( * ) Notice: Subject to any disclaimer, the term of this patent is extended or adjusted under 35 U.S.C. 154(b) by 271 days.

(21) Appl. No.: 17/749,887

(22) Filed: May 20, 2022

(65) Prior Publication Data

US 2022/0409639 A1    Dec. 29, 2022

Related U.S. Application Data

(60) Provisional application No. 63/215,140, filed on Jun. 25, 2021.

(51) Int. Cl.
| | | |
|---|---|---|
| *A61K 31/685* | (2006.01) | |
| *A61K 31/14* | (2006.01) | |
| *A61K 31/205* | (2006.01) | |
| *A61K 31/4748* | (2006.01) | |
| *A61K 31/51* | (2006.01) | |
| *A61K 33/06* | (2006.01) | |
| *A61P 27/04* | (2006.01) | |

(52) U.S. Cl.
CPC ............ *A61K 31/685* (2013.01); *A61K 31/14* (2013.01); *A61K 31/205* (2013.01); *A61K 31/4748* (2013.01); *A61K 31/51* (2013.01); *A61K 33/06* (2013.01); *A61P 27/04* (2018.01)

(58) Field of Classification Search
CPC .. A61K 31/14; A61K 31/205; A61K 31/4748; A61K 31/51; A61K 31/685; A61K 33/06; A61K 45/06; A61K 2300/00; A61K 31/221; A61K 31/465; A61K 9/0014; A61K 9/0031; A61K 9/0034; A61K 9/0048; A61P 9/00; A61P 25/00; A61P 27/00; A61P 27/02; A61P 27/04; Y02A 50/30

See application file for complete search history.

(56) References Cited

U.S. PATENT DOCUMENTS

| | | |
|---|---|---|
| 1,007,978 A | 11/1911 | Albert |
| 1,894,340 A | 1/1933 | Austin |
| 7,542,929 B2 | 6/2009 | Hanks et al. |
| 10,238,673 B2 | 3/2019 | Driscoll |
| 10,966,948 B2 | 4/2021 | Li et al. |
| 2015/0038851 A1 | 2/2015 | Hamrah et al. |
| 2017/0326163 A1 | 11/2017 | Driscoll |

(Continued)

OTHER PUBLICATIONS

Conrady, et al. "Review: The Lacrimal Gland and Its Role in Dry Eye" J Ophthalmol. 2016;2016:7542929. doi:10.1155/2016/7542929.

(Continued)

*Primary Examiner* — Savitha M Rao
(74) *Attorney, Agent, or Firm* — Edwin S. Flores; Daniel J. Chalker; Chalker Flores, LLP

(57) ABSTRACT

The present invention includes compositions and methods for the treatment or prevention of a disease or condition that causes dry eyes comprising: an effective amount of at least two active agents selected from: (1) at least one cholinesterase inhibitor; (2) at least one form of choline; (3) at least one form of carnitine; (4) at least one form of muscarinic agonist, sufficient to treat the disease or condition that causes dry eyes.

9 Claims, 2 Drawing Sheets

(56) References Cited

U.S. PATENT DOCUMENTS

2021/0154263 A1    5/2021    Dana et al.

OTHER PUBLICATIONS

Craig, et al. "TFOS DEWS II Report Executive Summary" Ocul Surf. Oct. 2017;15(4):802-812. doi: 10.1016/j.itos.2017.08.003. Epub Aug. 8, 2017. PMID: 28797892.

Dartt, DA. "Neural regulation of lacrimal gland secretory processes: relevance in dry eye diseases". Prog Retin Eye Res. 2009;28(3):155-177. doi:10.1016/j.preteyeres.2009.04.003.

Hagan, H. "Biomarkers of ocular surface disease using impression cytology" Biomarkers in Medicine. 2017 11:12, 1135-1147.

Hocevar A, T. M. "Parasympathetic nervous system dysfunction in primary Sjogrens Syndrome" Ann Rheum Dis, 702-704 (2003).

LeDoux, et al. "Parasympathetic innervation of the meibomian glands in rats" Invest Ophthalmol Vis Sci. Oct. 2001;42(11):2434-41. PMID: 11581180.

Li, et al. "Activities of autonomic neurotransmitters in Meibomian gland tissues are associated with menopausal dry eyes" Neural Regen Res, 2761-2769, (2012).

Passafaro, et al. "Cholinergic Autoantibodies from Primary Sjogrens Syndrome Inhibit Mucin Production via Phospholipase C and Cyclooxygenase-2 In the Rat Submandibular Gland" Dent Res J (Isfahan). 2011;8(3):138-145.

Reddy, et al. "Conjunctival impression cytology in dry eye states" Indian J Ophthalmol. Jan.-Mar. 1991;39(1):22-4. PMID: 1894340.

Singh, et al. "Impression cytology of the ocular surface" Br J Ophthalmol. 2005;89(12):1655-1659. doi:10.1136/bjo.2005.073916.

Tsuboi, et al. "New epitopes and function of anti-M3 muscarinic acetylcholine receptor antibodies in patients with Sjogrens syndrome" Clin Exp Immunol. 2010;162(1):53-61. doi:10.1111/j.1365-2249.2010.04188.x.

Vincent, A, M. S. "A report of the autonomic symptom profile in patients with fibromyaliga" J Clin Rheumatol, 106-108 (2014).

Zoukhri, et al. "Impaired neurotransmitter release from lacrimal and salivary gland nerves of a murine model of Sjogrens syndrome" Invest Ophthalmol Vis Sci. Apr. 2001;42(5):925-32. PMID: 11274068; PMCID: PMC3241007.

Cellini, et al. Ocular surface and intraocular inflammation are related in SS-1 and rheumatoid arthritis patients, Rheumatol Int., 2007, vol. 27, pp. 853-857; DOI 10.1007/s00296-007-0325-6. p. 854, col. 1, para 1-3; col. 2, para 1; p. 855, col. 1, para 1; Table 2; p. 856, col. 1, para 2.

Marube, et al. Impression cytology on conjunctiva and cornea in dry eye patients establishes a correlation between squamous metaplasia and dry eye clinical severity, European Journal of Ophthalmology, 2003, vol. 13 No. 2, pp. 115-127. abstract; p. 121, Table V; p. 124, col. 2, para 3.

United States Patent & Trademark Office (ISA) International Search Report and Written Opinion for PCT/US2022/030320 dated Aug. 16, 2022, 11 pp.

COMPOSITIONS AND METHODS FOR TREATING DRY EYE

CROSS-REFERENCE TO RELATED APPLICATIONS

This application claims priority to U.S. Provisional Application Ser. No. 63/215,140, filed Jun. 25, 2021, the entire contents of which are incorporated herein by reference.

TECHNICAL FIELD OF THE INVENTION

The present invention relates in general to the field of compositions and method for diseases, conditions, and symptoms related to dry eye.

STATEMENT OF FEDERALLY FUNDED RESEARCH

None.

BACKGROUND OF THE INVENTION

Without limiting the scope of the invention, its background is described in connection with treating dry eye.

U.S. Pat. No. 10,966,948, issued to Li, et al., is entitled "Compositions and methods for treating the eye" and is said to teach compositions comprising one or more extracts and/or compounds having retinol-like activity and properties and methods of using the compositions to treat the eye. The invention is said to include a method for treating the symptoms associated with dry eye, the method comprising the step of topically administering to a patient a composition comprising: i) a safe and effective amount of a compound and/or extract having retinol-like properties for treating dry eye and/or benefits for use in treating dry eye selected from one or more of: (a) one or more extracts from plants of the genera *Acronychia, Licaria,* and/or *Trigonella*; (b) one or more extracts of species of the genus *Actinomyces*; and (c) one or more compounds taught therein.

Work by the present inventor includes U.S. Pat. No. 10,238,673, entitled, "Methods and compositions for treatment of dry eye and correction of organ dysfunctions" and claims compositions and methods for treating certain conditions such as dry eye or dry mouth with a comprising a choline compound; a cholinesterase inhibitor; and Acetyl-L-Carnitine, wherein the composition is provided in an amount sufficient to treat dry eye or dry mouth.

United States Patent Publication No. 20210154263, filed by Reza, et al., entitled "Therapeutic compositions for the treatment of dry eye disease", is said to teach materials and methods for treating dry eye disease in a subject, that include treating dry eye disease (DED) in a human by administering a composition comprising at least one anti-lymphangiogenic agent and a pharmaceutically acceptable carrier to the eye of the human, in an amount effective to treat dry eye disease. The anti-lymphangiogenic agent is an inhibitor of VEGF-C- or VEGF-D-mediated signal transduction by VEGFR-2 or VEGFR-3.

There is an unmet need for the detection, improved treatment and prevention of diseases, conditions, and symptoms related to dry eye. This patent addresses those needs.

SUMMARY OF THE INVENTION

In one embodiment, the present invention includes a method for treating or preventing a disease or condition that causes dry eyes comprising: identifying a patient in need of treatment or prevention of dry eyes; and administering to the patient a composition comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes. In one aspect, the disease or condition is selected from Keratoconjunctivitis sicca, Aqueous deficiency dry eye disease (ADDE), allergies, Sjogren's syndrome, Evaporative Dry Eye (EDE), Vitamin A deficiency, blepharitis, meibomian gland disease, allergic conjunctivitis, pterygium, ocular symptoms of graft versus host disease, ocular allergy, atopic keratoconjunctivitis, vernal keratoconjunctivitis, uveitis, anterior uveitis, Bechet's disease, Steven Johnson syndrome, ocular cicatricial pemphigoid, chronic ocular surface inflammation caused by viral infection, herpes simplex keratitis, ocular rosacea, pinguecula, dry eyes associated with refractive surgery (or other ocular surgeries), due to damage to the pre- or post-ganglionic lacrimal nerve, associated with connective tissue disorders, in conjunction with chronic inflammatory conditions such as eosinophilic disorders. In another aspect, the dry eyes are caused by tear film instability, hyperosmolarity of tears, characterized by ocular surface inflammation, corneal damage, and neurosensory. In another aspect, the dry eyes are related to sex, gender, hormones, effects of sex steroids, hypothalamic-pituitary hormones, glucocorticoids, insulin, insulin-like growth factor 1, thyroid hormones, sex-related dry eyes including differences in parent-of-origin effects, X-chromosome gene dosage (ex: X-inactivation), genes in the non-recombing region of the Y-chromosome, from sex-specific autosomal factors and epigenetics. In another aspect, the Dry Eye Disease (DED) is meibomian gland dysfunction (MGD) related Dry Eye Disease (MDG-DED), MGD-DED with tear film lipid layer deficiency, a DED with a secondary evaporative element, DED due to blocking of the sensory drive to a lacrimal gland, DED due to trauma including, DED due to ocular or orbital surgery, or DED due to laser surgery, or DED due to LASIX surgery. In another aspect, a Dry Eye Disease (DED) is a genetic and/or acquired disorders of collagen (which may include Ehlers-Danlos syndrome, Marfan's syndrome, Loeys-Dietz syndrome, Stickler syndrome, fibrillin disorders, elastin disorders, Joint Hypermobility Syndrome) chronic infectious and/or fatigue syndrome including Chronic Fatigue Syndrome, COVID "Longhaulers" or Post-Acute Sequelae of SARS-CoV-2, Myalgic Encephalomyelitis, Post-Traumatic Stress Disorder, mild traumatic brain injury, Chronic Lyme disease, fibromyalgia; autoimmune disorders which may include multiple sclerosis, a vascular disease and a rheumatological disease. In another aspect, the dry eyes are associated with at least one of: Postural Orthostatic Tachycardia Syndrome ("POTS"), post-viral and post-infective autonomic dysfunction, chronic dry eyes, visual snow, and idiopathic dysautonomia (disorders of the autonomic nervous system), associated conditions include traumatic brain injury (TBI), Post Traumatic Stress Disorder (PTSD), post-infectious Postural Orthostatic Tachycardia Syndrome, inflammatory autonomic dysfunction and Inflammatory Postural Orthostatic Tachycardia Syndrome, genetic disorders of RCCX, CYP21A2, disorders of the TGF-beta cascade, TNX, SMAD), autoimmune disorders, abnormal hormones (androgens and estrogens), genetic disorders of tryptase (including hereditary alpha tryptasemia), Hyper IgE Syndrome, low immune system (low IgG, low IgA), Idiopathic Intracranial Hypertension (IIH), vascular oxidation (including that due to hemochromatosis and hemolysis), low nitric oxide, impaired release of acetylcholine, genetic disorders of the acetylcholine manufacturing cycle. In another aspect, the DED is iatrogenic, and the active agent is selected from: antihistamines, beta-blockers, antispasmodics, diuretics, some psychotropic drugs, cis-retinoic acid, polychlorinated biphenyls; skin disorders, acne rosacea, atopic dermatitis, seborrheic dermatitis, psoriasis, cicatricial conjunctival diseases such as trachoma, erythema multiforme and pemphigoid. In another aspect, the acetylcholinesterase inhibitor (cholinesterase inhibitor) is selected from pyridostigmine, donepezil, tacrine, galantamine, and memantine, carbamates, physostigmine, neostigmine, ambenonium, demecarium, rivastigmine, phenanthrene derivatives, galantamine, caffeine, rosmarinic acid, alpha-pinene, piperidines, tacrine, edrophonium, huperzine A, ladostigil, ungeremine, lactucopicrin, or acotiamide. In another aspect, the carnitine is selected from L-carnitine, Acetyl L-carnitine, L-carnitine L-tartrate, or Propionyl-L-carnitine. In another aspect, the muscarinic agonist is selected from at least one of: acetylcholine, carbachol, methacholine, bethanechol, muscarine, pilocarpine, oxotriemorine, cevimeline, aceclidine, arecoline, AF102B, AF150(S), or AF267B. In another aspect, the choline compound is selected from at least one of: lecithin, choline chloride, choline bitartrate, acetylcholine, glycerophosphocholine, phosphatidylcholine, sphingomyelin, cytidine-diphosphocholine, or alpha-glycerylphosphorylcholine. In another aspect, the composition comprises the two or more active agents selected from: 1, 5, 10, 20, 30, 40, 50, 60, 70, 75, 80, 90, 100, 110, 120, 125, 130, 140, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 3,750, or 4,000, or a range from 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, 1,500-2,000, 1,600 to 2,100, 1,700 to 2,200, 1,800 to 2,300, or 1,900 to 2,400, 2,500, 2,600, 2,700, 2,750, 2,800, 2,900, 3,000, 3,100, 3,200, 3,300, 3,400, 3,500, 3,600, 3,700, 3,750, 3,800, 3,900, and 4,000 mg of the choline compound; 0.001, 0.01, 0.1, 1, 2, 3, 4, 5, 6, 7, 8, 9, 10, 15, 20, 25, 30, 35, 40, 50 mg of the cholinesterase inhibitor; 0.001, 0.01, 0.1, 1, 2, 3, 4, 5, 6, 7, 8, 9, 10, 15, 20, 25, 30, 35, 40, 50, 60, 70, 75, 80, 90, 100, 110, 120, 125, 130, 140, 150 mg of the muscarinic agonist compound; 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 30 to 2,000, 40 to 2,300, 50 to 2,000, 60 to 1,500, 70 to 1,000, 80 to 750, 90 to 2,000, 200 to 2,000, 300 to 2,000, 400 to 2,000, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, 1,500-2,000 mg of the carnitine. In another aspect, the dose is 0.1, 0.5, 1, 5, 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg. In another aspect, the composition further comprises at least one of an antioxidant, magnesium, thiamin, or alpha lipoic acid, and if magnesium is provided it is selected from at least one of magnesium glycinate, magnesium oxide, magnesium chloride, magnesium lactate, magnesium carbonate, magnesium citrate, and/or magnesium threonate and is provided at between 0.1-800 mgs elemental magnesium; or if thiamin (thiamin/Vitamin B1) is provided it is provided at between 0.1-600 mg, or alpha-lipoic acid is 0.1-3,000 mg. In another aspect, the composition further comprises an antioxidant selected from Vitamin C (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Vitamin E (1, 5, 10, 20, 30, 40, 50, 60, 70, 80, 90, 100, 150, 200, 250, 270, 300, 350, 400, 450, 500, 540, 600, 700, 750, 800 mg), N-acetylcysteine (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Selenium (0.1, 0.2, 0.3, 0.5, 0.75, 1, 5, 10, 20, 30, 40, 50, 60, 70, 80, 90, 100, 150, 200, 250, 270, 300, 350, 400 mcg), Curcumin (0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg). In another aspect, the composition is adapted to be administered prenatally, orally, intravenously, intraperitoneally, intranasally, intrapulmonary, subcutaneously, intracutaneously, or intramuscularly.

In another embodiment, the present invention includes a composition for treating or preventing a disease or condition that causes dry eyes comprising: an effective amount of at least two active agents selected from: (1) at least one cholinesterase inhibitor; (2) at least one form of choline; (3) at least one form of carnitine; (4) at least one form of muscarinic agonist, sufficient to treat the disease or condition that causes dry eyes. In one aspect, the acetylcholinesterase inhibitor (cholinesterase inhibitor) is selected from pyridostigmine, donepezil, tacrine, galantamine, and memantine, carbamates, physostigmine, neostigmine, ambenonium, demecarium, rivastigmine, phenanthrene derivatives, galantamine, caffeine, rosmarinic acid, alpha-pinene, piperidines, tacrine, edrophonium, huperzine A, ladostigil, ungeremine, lactucopicrin, or acotiamide. In another aspect, the carnitine is selected from L-carnitine, Acetyl L-carnitine, L-carnitine L-tartrate, or Propionyl-L-carnitine. In another aspect, the muscarinic agonist is selected from at least one of: acetylcholine, carbachol, methacholine, bethanechol, muscarine, pilocarpine, oxotriemorine, cevimeline, aceclidine, arecoline, AF102B, AF150 (S), or AF267B. In another aspect, the choline compound is selected from at least one of: lecithin, choline chloride, choline bitartrate, acetylcholine, glycerophosphocholine, phosphatidylcholine, sphingomyelin, cytidine-diphosphocholine, or alpha-glycerylphosphorylcholine. In another aspect, the composition comprises the two or more active agents selected from: 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 3,750, or 4,000, or a range from 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, 1,500-2,000, 1,600 to 2,100, 1,700 to 2,200, 1,800 to 2,300, or 1,900, 2,400, 2,500-2,600, 2,700-2,750, 2,800-2,900, 3,000-3,100, 3,200-3,300, 3,400-3,500, 3,600-3,700, 3,750-3,800, and 3,900-4,000 mg of the choline compound; 0.001, 0.01, 0.1, 1, 2, 3, 4, 5, 6, 7, 8, 9, 10, 15, 20, 25, 30, 35, 40, 50 mg of the cholinesterase inhibitor; 0.001, 0.01, 0.1, 1, 2, 3, 4, 5, 6, 7, 8, 9, 10, 15, 20, 25, 30, 35, 40, 50, 60, 70, 80, 90, 100, 110, 120, 125, 130, 140, 150 mg of the muscarinic agonist compound; 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 30 to 2,000, 40 to 2,300, 50 to 2,000, 60 to 1,500, 70 to 1,000, 80 to 750, 90 to 2,000, 200 to 2,000, 300 to 2,000, 400 to 2,000, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, 1,500-2,000 mg of the carnitine. In another aspect, the dose is 0.1, 0.5, 1, 5, 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg. In another aspect, the composition further comprises at least one of an antioxidant, magnesium, thiamin, or alpha lipoic acid, and if magnesium is provided it is selected from at least one of magnesium glycinate, magnesium oxide, magnesium chloride, magnesium lactate, magnesium carbonate, magnesium citrate, and/or magnesium threonate and is provided at between 0.1, 0.5, 1, 5, 10, 20, 30, 40, 50, 60, 70, 80, 90, 100, 150, 200, 250, 270, 300, 350, 400, 450, 500, 600, 700, 750, 800 mgs elemental magnesium; or if thiamin (thiamin/Vitamin B1) is provided it is provided at between 0.1-600 mg, or alpha-lipoic acid is 0.1-3,000 mg. In another aspect, the composition further comprises an antioxidant selected from Vitamin C (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Vitamin E (1, 5, 10, 20, 30, 40, 50, 60, 70, 80, 90, 100, 150, 200, 250, 270, 300, 350, 400, 450, 500, 540, 600, 700, 750, 800 mg), N-acetylcysteine (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Selenium (0.1, 0.2, 0.3, 0.5, 0.75, 1, 5, 10, 20, 30, 40, 50, 60, 70, 80, 90, 100, 150, 200, 250, 270, 300, 350, 400 mcg), Curcumin (0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg). In another aspect, the composition is adapted to be administered prenatally, orally, intravenously, intraperitoneally, intranasally, intrapulmonary, subcutaneously, intracutaneously, or intramuscularly. In another aspect, the disease or condition is selected from Keratoconjunctivitis sicca, Aqueous deficiency dry eye disease (ADDE), allergies, Sjogren's syndrome, Evaporative Dry Eye (EDE), Vitamin A deficiency, blepharitis, meibomian gland disease, allergic conjunctivitis, pterygium, ocular symptoms of graft versus host disease, ocular allergy, atopic keratoconjunctivitis, vernal keratoconjunctivitis, uveitis, anterior uveitis, Bechet's disease, Steven Johnson syndrome, ocular cicatricial pemphigoid, chronic ocular surface inflammation caused by viral infection, herpes simplex keratitis, ocular rosacea, pinguecula, dry eyes associated with refractive surgery (or other ocular surgeries), due to damage to the pre- or post-ganglionic lacrimal nerve, associated with connective tissue disorders, in conjunction with chronic inflammatory conditions such as eosinophilic disorders. In another aspect, the dry eyes are associated with at least one of: Postural Orthostatic Tachycardia Syndrome ("POTS"), post-viral and post-infective autonomic dysfunction, COVID "Longhaulers" or Post-Acute Sequelae of SARS-CoV-2, Myalgic Encephalomyelitis, chronic dry eyes, visual snow, and idiopathic dysautonomia (disorders of the autonomic nervous system), chronic conditions associated conditions include traumatic brain injury (TBI), Post Traumatic Stress Disorder (PTSD), post-infectious Postural Orthostatic Tachycardia Syndrome, inflammatory autonomic dysfunction and Inflammatory Postural Orthostatic Tachycardia Syndrome, genetic disorders of RCCX, CYP21A2, MCP-1, disorders of the TGF-beta cascade, TNX, SMAD), autoimmune disorders, abnormal hormones (androgens and estrogens), genetic disorders of tryptase (including hereditary alpha tryptasemia), Hyper IgE Syndrome, low immune system (low IgG, low IgA), Idiopathic Intracranial Hypertension (IIH), impaired release of acetylcholine, genetic disorders of the acetylcholine manufacturing cycle. In another aspect, the dry eyes are caused by tear film instability, hyperosmolarity of tears, characterized by ocular surface inflammation, corneal damage, and neurosensory abnormalities; it may involve increased ocular pain and sensitization, neuropathic pain. In another aspect, the dry eyes are related to sex, gender, hormones, effects of sex steroids, hypothalamic-pituitary hormones, glucocorticoids, insulin, insulin-like growth factor 1, thyroid hormones, Sex-related dry eyes including differences in parent-of-origin effects, X-chromosome gene dosage (ex: X-inactivation), genes in the non-recombing region of the Y-chromosome, from sex-specific autosomal factors and epigenetics. In another aspect, the Dry Eye Disease (DED) is meibomian gland dysfunction (MGD) related Dry Eye Disease (MDG-DED), MGD-DED with tear film lipid layer deficiency, a DED with a secondary evaporative element, DED due to blocking of the sensory drive to a lacrimal gland, DED due to trauma including, DED due to surgery, or DED due to laser surgery, or DED due to LASIX surgery. In another aspect, the DED is a genetic and/or acquired disorders of collagen (which may include Ehlers-Danlos syndrome, Marfan's syndrome, Loeys-Dietz syndrome, Stickler syndrome, fibrillin disorders, elastin disorders, Joint Hypermobility Syndrome) chronic infectious and/or fatigue syndrome including Chronic Fatigue Syndrome, COVID "Longhaulers" or Post-Acute Sequelae of SARS-CoV-2, Myalgic Encephalomyelitis, Post-Traumatic Stress Disorder, mild traumatic brain injury, chronic Lyme disease, fibromyalgia; autoimmune disorders which may include multiple sclerosis, a vascular disease and a rheumatological disease. In another aspect, the DED is iatrogenic, and the active agent is selected from: antihistamines, beta-blockers, antispasmodics, diuretics, some psychotropic drugs, cis-retinoic acid, polychlorinated biphenyls; skin disorders, acne rosacea, atopic dermatitis, seborrheic dermatitis, psoriasis, cicatricial conjunctival diseases such as trachoma, erythema multiforme and pemphigoid.

In another embodiment, the present invention includes a method for using conjunctival cytology of a patient suspected, to detect neurologic chronic dry eye prior to damage to a lacrimal gland, comprising: obtaining a sample from the palpebral conjunctiva; staining the sample to detect inflammatory cells; and determining that the patient has neurologic dry eyes due to the presence of inflammatory cells near the lacrimal nerve, wherein epithelial cells in the palpebral conjunctiva have a normal nucleus to cytoplasm ratio, and wherein the inflammatory cells cause a lacrimal nerve insufficiency that causes the chronic dry eyes. In one aspect, the sample is examined for an increase in inflammatory cells in the conjunctiva. In another aspect, if the patient has the lacrimal nerve insufficiency, treating the patient with a composition comprising at least two active agents selected from: (1) at least one cholinesterase inhibitor; (2) at least one form of choline; (3) at least one form of carnitine; (4) at least one form of muscarinic agonist, sufficient to treat the disease or condition that causes dry eyes. In another aspect, the method further comprises treating the dry eye, wherein if the patient has the lacrimal nerve insufficiency, treating the patient with a composition comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes. In another aspect, the composition further comprises at least one of 0.1, 0.5, 1, 5, 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg. In another aspect, the composition further comprises at least one of an antioxidant, magnesium thiamin, or alpha lipoic acid, and if magnesium is provided it is selected from at least one of magnesium glycinate, magnesium oxide, magnesium chloride, magnesium lactate, magnesium carbonate, magnesium citrate, and/or magnesium threonate and is provided at between 0.1, 0.5, 1, 5, 10, 20, 30, 40, 50, 60, 70, 80, 90, 100, 150, 200, 250, 270, 300, 350, 400, 450, 500, 600, 700, 750, 800 mgs elemental magnesium; or if thiamin (thiamin/Vitamin B1) is provided it is provided at between 0.1-600 mg, or alpha-lipoic acid is 0.1-3,000 mg. In another aspect, the composition further comprises an antioxidant selected from Vitamin C (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Vitamin E (1, 5, 10, 20, 30, 40, 50, 60, 70, 80, 90, 100, 150, 200, 250, 270, 300, 350, 400, 450, 500, 540, 600, 700, 750, 800 mg), N-acetylcysteine (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Selenium (0.1, 0.2, 0.3, 0.5, 0.75, 1, 5, 10, 20, 30, 40, 50, 60, 70, 80, 90, 100, 150, 200, 250, 270, 300, 350, 400 mcg), Curcumin (0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg).

In another embodiment, the present invention includes a method for treating at least one of chronic dry eye prior to damage to a lacrimal gland, neurological dry eye, or dry corneas comprising: obtaining a sample from the palpebral conjunctiva of a patient; staining the sample to detect inflammatory cells; and determining that the patient has neurologic dry eyes due to the presence of inflammatory cells near the lacrimal nerve, wherein epithelial cells in the palpebral conjunctiva have a normal nucleus to cytoplasm ratio, and wherein the inflammatory cells cause a lacrimal nerve insufficiency that causes the chronic dry eyes; wherein if the patient has lacrimal nerve insufficiency, providing the patent with a composition comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes. In another aspect, the sample is examined for an increase in inflammatory cells in the conjunctiva; or measuring pupil size before and after administration of the composition, wherein above-average pupil size becomes smaller with treatment of the compound and is diagnostic of neurological dry eye; wherein the symptoms and signs of dry eyes and low tear production by either acinar cells of the lacrimal gland or cells of meibomian glands as determined by at least one of: tear film instability, hyperosmolarity of tears, ocular surface inflammation, corneal damage, neurosensory abnormalities; increased ocular pain and sensitization, neuropathic pain, light sensitivity, decreased accommodation, fluctuating vision, or pupils that are larger than average, which respond to treatment with the composition. In another aspect, if the patient has the lacrimal nerve insufficiency, treating the patient with a composition comprising at least two active agents selected from: (1) at least one cholinesterase inhibitor; (2) at least one form of choline; (3) at least one form of carnitine; (4) at least one form of muscarinic agonist, sufficient to treat the disease or condition that causes dry eyes. In another aspect, if the patient has the lacrimal nerve insufficiency, the composition activates muscarinic receptors on acinar cells of a lacrimal gland, accessory lacrimal glands, or both to stimulate tear production without vagus nerve stimulation. In another aspect, the composition further comprises at least one of 0.1, 0.5, 1, 5, 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg. In another aspect, the composition further comprises at least one of an antioxidant, magnesium thiamin, or alpha lipoic acid, and if magnesium is provided it is selected from at least one of magnesium glycinate, magnesium oxide, magnesium chloride, magnesium lactate, magnesium carbonate, magnesium citrate, and/or magnesium threonate and is provided at between 0.1, 0.5, 1, 5, 10, 20, 30, 40, 50, 60, 70, 80, 90, 100, 150, 200, 250, 270, 300, 350, 400, 450, 500, 600, 700, 750, 800 mgs elemental magnesium; or if thiamin (thiamin/Vitamin B1) is provided it is provided at between 0.1-600 mg, or alpha-lipoic acid is 0.1-3,000 mg. In another aspect, the composition further comprises an antioxidant selected from Vitamin C (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Vitamin E (1, 5, 10, 20, 30, 40, 50, 60, 70, 80, 90, 100, 150, 200, 250, 270, 300, 350, 400, 450, 500, 540, 600, 700, 750, 800 mg), N-acetylcysteine (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Selenium (0.1, 0.2, 0.3, 0.5, 0.75, 1, 5, 10, 20, 30, 40, 50, 60, 70, 80, 90, 100, 150, 200, 250, 270, 300, 350, 400 mcg), Curcumin (0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg). In one aspect, the composition stimulates at least one of: muscarinic receptors of ocular pupils, lacrimal gland, or meibomian glands.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
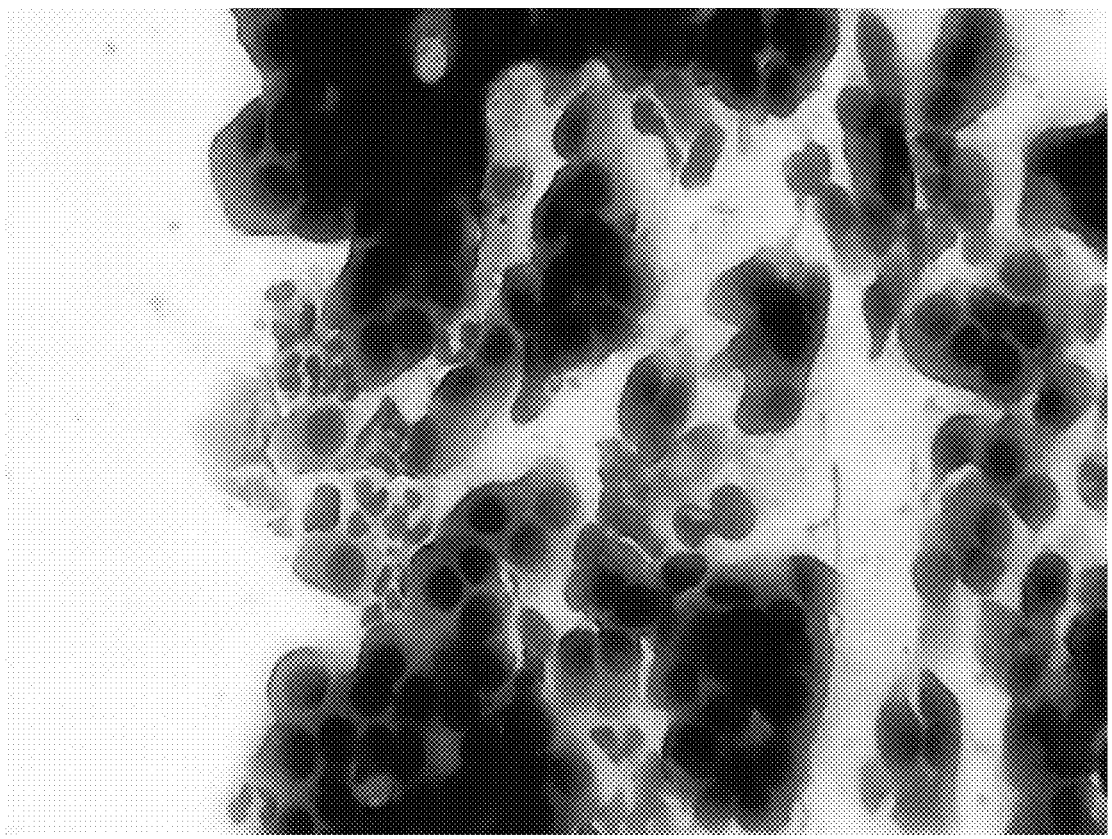
FIG. 1 shows neutrophils obtained from chronic dry eye patient 11, Table 3.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Chronic dry eye, often accompanied by dry mouth, causes significant morbidity and even disability, and yet treatment is limited to a symptomatic approach, or it is limited to specific aspects of inflammation, leaving many patients to suffer with continued symptoms.

The production of the tear film is under tight neurological control and the parasympathetic nervous system is the major autonomic system that promotes both the aqueous layer of tears by the lacrimal gland, and the oil layer of tears by the meibomian glands. Afferent sensory nerves in the conjunctiva and cornea stimulate the parasympathetic nervous system (with a minor contribution from the sympathetic nervous system) that innervates the lacrimal gland and meibomian glands. The release of the neurotransmitter involved in the parasympathetic nervous system (acetylcholine) can be dramatically affected by inflammatory cells, inflammatory cytokines, and inflammatory chemokines.

Lymphocytes are known to mediate ocular surface inflammation. Lymphocytes have been shown to block the release of acetylcholine from the lacrimal nerve in Sjogren's syndrome. This results in dramatic dry eyes, despite a functioning lacrimal gland. Studies have shown that more than half of patients with Sjogren's syndrome tested do not show antibodies to these lacrimal receptors. These studies have shown that approximately 50% of the acinar cells of the lacrimal gland are still viable in patients with advanced Sjogren's syndrome, and yet the patients display dramatic dry eyes.

The present invention includes compositions and method for treating or preventing dry eyes comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes. It was recognized herein that cholinergic agonists include both muscarinic cholinergic agonists and nicotinic cholinergic agonists. Thus, as used herein, the phrases "muscarinic agonists" and "cholinergic agonists with muscarinic properties" are used interchangeably. In certain aspect, the muscarinic agonist is selected such that it does not stimulate the (nicotinic) vagus nerve.

A dosage unit for use of the composition of the present invention may be a single compound or mixtures thereof with other compounds. The compounds may be mixed together, form ionic or even covalent bonds. The composition of the present invention may be administered in oral, intravenous (bolus or infusion), intraperitoneal, subcutaneous, transdermal, transcutaneous, intrapulmonary, intranasal, suppositories, or intramuscular form, including prenatally, all using dosage forms well known to those of ordinary skill in the pharmaceutical arts, vaginal suppository or anal suppository). Depending on the particular location or method of delivery, different dosage forms, e.g., tablets, capsules, pills, powders, granules, liquids, elixirs, tinctures, suspensions, syrups, and emulsions may be used to provide the composition of the present invention to a patient in need of therapy for a medical condition or symptom. The composition may also be administered as any one of known salt forms.

The composition of the present invention is typically administered in a mixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for the particular form for oral, vaginal, rectal, topical, transdermal, subcutaneous, intravenous injection or parenteral administration. While the composition may be administered alone, it will generally be provided in a stable salt form mixed with a pharmaceutically acceptable carrier. The carrier may be solid or liquid, depending on the type and/or location of administration selected.

For example, the composition may be included in a tablet or capsule. Tablets or capsules may contain, e.g., suitable binders, lubricants, disintegrating agents, coloring agents, flavoring agents, flow-inducing agents and/or melting agents. For example, oral administration may be in a dosage unit form of a tablet, gelcap, caplet or capsule, the active drug component being combined with a non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol, mixtures thereof, and the like. Suitable binders for use with the present invention include: starch, gelatin, natural sugars (e.g., glucose or beta-lactose), corn sweeteners, natural and synthetic gums (e.g., acacia, tragacanth or sodium alginate), carboxymethylcellulose, polyethylene glycol, waxes, and the like. Lubricants for use with the invention may include: sodium oleate, sodium stearate, magnesium stearate, sodium benzoate, sodium acetate, sodium chloride, mixtures thereof, and the like. Disintegrators may include: starch, methyl cellulose, agar, bentonite, xanthan gum, mixtures thereof, and the like.

The composition may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The composition may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the composition may be coupled one or more biodegradable polymers to achieve controlled release of the composition, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In one embodiment, gelatin capsules (gelcaps) may include the composition and powdered carriers, such as lactose, starch, cellulose derivatives, magnesium stearate, stearic acid, and the like. Like diluents may be used to make compressed tablets. Both tablets and capsules may be manufactured as immediate-release, mixed-release or sustained-release formulations to provide for a range of release of medication over a period of minutes to hours. Compressed tablets may be sugar coated or film coated to mask any unpleasant taste and protect the tablet from the atmosphere. An enteric coating may be used to provide selective disintegration in, e.g., the gastrointestinal tract.

For oral administration in a liquid dosage form, the oral drug components may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like.

Liquid dosage forms for oral administration may also include coloring and flavoring agents that increase patient acceptance and therefore compliance with a dosing regimen. In general, water, a suitable oil, saline, aqueous dextrose (e.g., glucose, lactose and related sugar solutions) and glycols (e.g., propylene glycol or polyethylene glycols) may be used as suitable carriers for parenteral solutions. Solutions for parenteral administration include generally, a water-soluble salt of the active ingredient, suitable stabilizing agents, and if necessary, buffering salts. Antioxidizing agents such as sodium bisulfate, sodium sulfite and/or ascorbic acid, either alone or in combination, are suitable stabilizing agents. Citric acid and its salts and sodium EDTA may also be included to increase stability. In addition, parenteral solutions may include pharmaceutically acceptable preservatives, e.g., benzalkonium chloride, methyl- or propylparaben, and/or chlorobutanol. Suitable pharmaceutical carriers are described in Remington's Pharmaceutical Sciences, Mack Publishing Company, a standard reference text in this field, relevant portions incorporated herein by reference.

For direct delivery to the nasal passages, sinuses, mouth, throat, esophagus, trachea, lungs and alveoli, the composition (excepting nicotine) may also be delivered as an intranasal form via use of a suitable intranasal vehicle. For dermal and transdermal delivery, the composition may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of composition may include the following forms.

Capsules. Capsules may be prepared by filling standard two-piece hard gelatin capsules each with 1, 5, 10, 20, 30, 40, 50, 60, 70, 80, 90, 100, 110, 120, 125, 130, 140, 150, 175, 200, 225, 250, 275, 300, 325, 350, 375, 400, 425, 450, 475, or 500 milligrams of powdered active ingredient (e.g., the composition can be taken QD, BID, or TID, the daily dose may comprise: the composition comprises the two or more active agents selected from: a choline compound (such as lecithin, choline chloride, choline bitartrate, acetylcholine, glycerophosphocholine, phosphatidylcholine, sphingomyelin, cytidine-diphosphocholine, or alpha-glycerylphosphorylcholine), e.g., choline at 1 mg to 4,000 mg, lecithin at 1 mg to 4 grams, or L-alpha glycerylphosphorylcholine at 0.1 mg to 2,400 mg; 1 mcg to 150 mg of the muscarinic agonist is selected from at least one of: acetylcholine, carbachol, methacholine, bethanechol, muscarine, pilocarpine, oxotriemorine, cevimeline, aceclidine, arecoline, AF102B, AF150(S), or AF267B, 1 mcg to 50 mg of the acetylcholinesterase inhibitor (or cholinesterase inhibitor) is selected from carbamates, physostigmine, neostigmine, pyridostigmine, ambenonium, demecarium, rivastigmine, phenanthrene derivatives, galantamine, caffeine (dose 1 mg-500 mg), rosmarinic acid, alpha-pinene, piperidines, donepezil, tacrine, edrophonium, huperzine A, ladostigil, ungeremine, lactucopicrin, memantine, or acotiamide, e.g., the dose of the cholinesterase inhibitor is 0.001, 0.01, 0.1, 1, 2, 5, 10, 15, 20, 25, 30, 35, 40, or 50 mg; or 1 mg to 2,000 mg of the carnitine selected from L-carnitine, Acetyl L-carnitine, L-carnitine L-tartrate, or Propionyl-L-carnitine. The choline compound can be selected from, e.g., at least one of: lecithin, choline chloride, choline bitartrate, acetylcholine, glycerophosphocholine, phosphatidylcholine, sphingomyelin, cytidine-diphosphocholine, or alpha-glycerylphosphorylcholine.

The dose of the choline compound is 1, 5, 10, 20, 30, 40, 50, 60, 70, 75, 80, 90, 100, 110, 120, 125, 130, 140, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 3,750, or 4,000, or a range from 30 to 2,400, 40 to 2,300, 50 to 2,000, 60 to 1,500, 70 to 1,000, 80 to 750, 90 to 2,400, 200 to 2,300, 300 to 2,200, 400 to 2,100, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, 1,500-2,000, 1,600 to 2,100, 1,700 to 2,200, 1,800 to 2,300, or 1,900 to 2,400, 2,500, 2,600, 2,700, 2,750, 2,8000, 2,900, 3,000, 3,100, 3,200, 3,300, 3,400, 3,500, 3,600, 3,700, 3,730, 3,800, 3,900, and 4,000 mg.

The dose of the carnitine is 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 30 to 2,000, 40 to 2,300, 50 to 2,000, 60 to 1,500, 70 to 1,000, 80 to 750, 90 to 2,000, 200 to 2,000, 300 to 2,000, 400 to 2,000, 500 to 2,000, 600 to 1,900, 700 to 1,800, 800 to 1,700, 900 to 1,600, 1,000 to 1,500, 1,100 to 1,400, 1,200 to 1,300, 1,300 to 1,500, or 1,500-2,000 mg.

The dose of the muscarinic agonist compound is 0.001, 0.01, 0.1, 1, 2, 3, 4, 5, 6, 7, 8, 9, 10, 15, 20, 25, 30, 35, 40, 50, 60, 75, 80, 90, 100, 110, 120, 125, 130, 140 or 150 mg.

The composition optionally comprises at least one of thiamin, Magnesium, alpha-lipoic acid. The dose of thiamin is 0.1, 0.5, 1, 5, 10, 20, 30, 40, 50, 60, 70, 80, 90, 100, 150, 200, 250, 300, 350, 400, 450, 500, 550, 600 mg. The dose of Magnesium is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, or 800 mg. The dose of alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg.

Antioxidants:

Combining the above ingredients with a special blend of antioxidants improves dry eye symptoms and presentation in a synergistic way. It was found that the response was dramatic and repeatable. Further, it was not intuitive that this can be accomplished orally.

With chronic inflammation, chronic oxidation is always a consequence. Cytology studies revealed abnormal numbers of lymphocytes and neutrophils, which produce oxidative chemicals (Reactive Oxygen Species). Studies show that oral antioxidants can help with dry eyes, but the inventor did not find this effect to be significant when used alone. However, when combined with any two of: a choline, an acetylcholinesterase inhibitor, a carnitine, and a muscarinic agonist, the response was strongly positive and synergistic.

Non-limiting examples of antioxidants for use with the present invention includes, e.g., Vitamin C (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Vitamin E (1, 5, 10, 20, 30, 40, 50, 60, 70, 80, 90, 100, 150, 200, 250, 270, 300, 350, 400, 450, 500, 540, 600, 700, 750, 800 mg), N-acetylcysteine (1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg), Selenium (0.1, 0.2, 0.3, 0.5, 0.75, 1, 5, 10, 20, 30, 40, 50, 60, 70, 80, 90, 100, 150, 200, 250, 270, 300, 350, 400 mcg), Alpha-lipoic acid (0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg), Curcumin (liposomal or with piperine to assist absorption)—(0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg), The combined dose of antioxidants can be 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg. Other non-limiting examples of antioxidants for use with the present invention include: Vitamin A, Quercetin, Tumeric, Zinc, Copper, Manganese, Capsa, Bilirubin, Citric acid, oxalic acid, and phytic acid, Lipoic acid, Alpha-carotene Astaxanthin, Beta-carotene, Canthaxanthin, Cryptoxanthin, Lutein, Lycopene, Zeaxanthin, Flavonoids, Apigenin, Luteolin, Tangeritin, Flavonols, Isorhamnetin, Kaempferol, Myricetin, Proanthocyanidins, Quercetin, rutin, Flavones, Eriodictyol, Hesperetin, hesperidin, Naringenin, Flavanols and their polymers, Catechin, gallocatechin and their corresponding gallate esters, Epicatechin, epigallocatechin and their corresponding gallate esters, Theaflavin its gallate esters, Thearubigins, Isoflavone phytoestrogens, Daidzein, Genistein, Glycitein, Stilbenoids, Resveratrol, Pterostilbene, Anthocyanins, Cyanidin, Delphinidin, Malvidin, Pelargonidin, Peonidin, Petunidin, Phenolic acids and their esters, Chicoric acid, Chlorogenic acid, Cinnamic acid, Ellagic acid, Ellagitannins, Gallic acid, Gallotannins, Rosmarinic acid in rosemary, oregano, lemon balm, sage, and marjoram, Salicylic acid, Other nonflavonoid phenolics, Curcumin, Flavonolignans—e.g. silymarin, Xanthones, Eugenol.

Soft Gelatin Capsules. A mixture of active ingredient is dissolved in a digestible oil such as soybean oil, cottonseed oil or olive oil. The active ingredient is prepared and injected by using a positive displacement pump into gelatin to form soft gelatin capsules containing, e.g., 1, 5, 10, 20, 30, 40, 50, 60, 70, 80, 90, 100, 150, 200, 250, 270, 300, 350, 400, 450, or 500 milligrams of the active ingredient. The capsules are washed and dried.

Tablets. A large number of tablets are prepared by conventional procedures so that the dosage unit was 1, 5, 10, 20, 30, 40, 50, 60, 70, 80, 90, 100, 150, 200, 250, 270, 300, 350, 400, 450, or 500 milligrams of active ingredient, 0.2 milligrams of colloidal silicon dioxide, 5 milligrams of magnesium stearate, 50-275 milligrams of microcrystalline cellulose, 11 milligrams of starch and 98.8 milligrams of lactose. Appropriate coatings may be applied to increase palatability or delay absorption.

Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

To provide an effervescent tablet appropriate amounts of, e.g., monosodium citrate and sodium bicarbonate, are blended together and then roller compacted, in the absence of water, to form flakes that are then crushed to give granulates. The granulates are then combined with the active ingredient, drug and/or salt thereof, conventional beading or filling agents and, optionally, sweeteners, flavors and lubricants.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration.

Suspension. An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

For mini-tablets, the active ingredient is compressed into a hardness in the range 6 to 12 Kp. The hardness of the final tablets is influenced by the linear roller compaction strength used in preparing the granulates, which are influenced by the particle size of, e.g., the monosodium hydrogen carbonate and sodium hydrogen carbonate. For smaller particle sizes, a linear roller compaction strength of about 15 to 20 KN/cm may be used.

For rectal and vaginal routes of administration, the composition of the present invention can be formulated as solutions, retention enemas, suppositories or ointments containing conventional suppository bases such as cocoa butter or other glycerides. Suppositories may also include about 0.5% to about 50% of a compound of the invention, disposed in a polyethylene glycol (PEG) carrier, for example, PEG 1000 (96%) and PEG 4000 (4%).

An exemplary transdermal device generally includes a reservoir defined by an impermeable backing layer and a membrane. The backing layer and the membrane are joined together about the outer periphery of the device. These layers may be joined by an adhesive, a heat seal, or the like. The transdermal device may also include an adhesive layer to attach the device to the skin of a subject. A release liner will generally cover the adhesive that the user removes prior to use of the device to expose adhesive layer.

Backing layer defines the distal side of the patch, that is, the side furthest from the skin in use. The backing layer functions as the primary structural element of the device and provides the device with its mechanical properties, e.g., flexibility. The backing layer serves as a protective, impermeable covering to prevent loss of the particles containing the active compound(s) in the reservoir. Suitable backing materials include commercially available films for medical use, such as those supplied by 3M corporation, Dow Chemical or Fasson Medical Industries. Typical backing materials are made from polyester or the like and may be pigmented or metallized.

The reservoir is defined generally by the space or gap between the backing layer and the membrane, provides a storage structure in which to retain the suspension of particles containing the active compound(s) to be administered. One side of the reservoir is generally defined by a highly porous member that retains the formulation within the reservoir, i.e., it deters bulk flow of the formulation out of the reservoir, but allows passage of the formulation from the reservoir into the skin. Materials suitable for use as membrane include non-woven fabrics such as nonwoven polyesters, polyethylene, polypropylene and other synthetic polymers. The material is heat or otherwise sealable to the backing layer to provide a barrier to transverse flow of reservoir contents.

Adhesive layer is the means by which the device is affixed to the skin. This layer is made from a pharmaceutically acceptable pressure sensitive adhesive, such as polydimethylsiloxane, polyisobutylene, polyacrylate, polyurethane and the like. It will be appreciated that the adhesive layer can also be a peripheral, or rim, adhesive layer.

The transdermal device containing the particles containing active compound(s) may also include a peel strip or release liner to cover the surface of the adhesive layer and to prevent loss of reservoir contents during storage. Prior to use, the release liner is removed from the device. The release liner is typically a material impermeable to the reservoir contents, for example polyethylene terephthalate, and is releasable usually by treatment with a silicone or fluorocarbon.

Transdermal devices generally include a backing layer, a membrane and a peripheral adhesive layer. The backing layer and membrane may be glued or heat-sealed about the periphery of the device. A reservoir defined by the space between the backing layer and the membrane provides for storage of particles containing the active compound(s) to be administered transdermally. The peripheral adhesive layer may be applied directly to backing layer. A release liner protects the device during storage.

The contents of the reservoir may even be in direct contact with the skin when the device is affixed to a subject. The reservoir in this device is composed of an absorbent sponge or a porous, highly permeable polymer. Materials suitable for the reservoir include polyurethane, polyethylene or polypropylene materials. An impermeable backing layer prevents loss of reservoir contents through the distal, top side of the device. The backing layer is coated on its distal side with an adhesive overlay, which is protected by a backing or polymer layer. Prior to use, the peripheral edge of the adhesive overlay is exposed by peeling a release liner and an impermeable protective strip from the proximal, skin side of the device. The transdermal delivery device may be adhesively attached to the skin of the user, although other methods for attaching the device to the skin are contemplated and suitable, e.g., an elastic arm band or an adjustable belt.

Transdermal device membranes are generally porous, highly permeable membranes with minimal resistance to diffusion of the reservoir contents, relative to the skin. At the same time, the membrane functions to prevent bulk flow of the particles containing the active compound(s) in the reservoir. Materials suitable for use as a membrane include hydrophilic and hydrophobic fabrics, cloths and polymer films having a porosity suitable for retaining the particles containing the active compound(s). Such materials may be nonwoven or woven, yet having a defined pore size. It will be appreciated that the membrane can be selected to provide more or less diffusional resistance as desired. For example, to design a device where the membrane is rate controlling, rather than the skin, a membrane with a tighter weave or smaller pore size can be selected.

Kits. The present invention also includes pharmaceutical kits useful, for example, for the treatment of medical conditions associated with the diseases discussed hereinabove, which comprise one or more containers containing a pharmaceutical composition comprising a therapeutically effective amount of the components of the composition. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The present inventor recognized that what is lacking for chronic dry eye patients is a compound that can replace the acetylcholine, blocked from release by inflammatory cells and their associated chemicals in the synapse of the ocular parasympathetic nervous system, sufficiently to allow stimulation of either the postganglionic lacrimal nerve or the receptors stimulated by this system. In certain embodiments, the present invention can stimulate the muscarinic receptors of the postganglionic lacrimal nerve (or the muscarinic receptors on the secretory globular acinar cells of the lacrimal gland served by the postganglionic parasympathetic lacrimal nerve) as well as the muscarinic receptors on the meibomian glands, without causing drug side-effects and without unnecessary stimulation of the (nicotinic) vagus nerve with its accompanying side effects, improving tear production and eliminating dry eyes. This invention also supports the oily layer of tears that helps to prevent evaporative dry eye.

This invention simultaneously eliminates dry mouth (in addition to dry eyes) by activating the muscarinic receptors in the salivary gland ductal tree, evoking the secretion of saliva by acinar cells.

Drugs available today designed to promote parasympathetic lacrimal nerve function are limited by significant side-effects and are not utilized for dry eyes for this reason.

Carbachol results in miosis that can diminish ocular focus; it is not well absorbed in the gastrointestinal tract (and is therefore reserved as an ocular topical medication used to lower intraocular pressure or is used as an injectable). Carbachol stimulates both muscarinic and nicotinic receptors (meaning unwanted nicotinic vagal side-effects can result).

Pilocarpine causes miosis, blurred vision, pupillary spasms; topically, it also results in burning and stinging.

Cevimeline causes bladder pain, nausea, vomiting, diarrhea, sweating, rash, headache, runny nose, drowsiness, hot flashes, blurred vision, difficulty sleeping.

Bethanechol's side effects include dizziness, drowsiness, lightheadedness, headache, nausea, vomiting, abdominal cramps/pain, diarrhea, increased salivation or urination, headache, slow heart rate followed by fast heart rate, and sweating. This muscarinic agonist is relatively selective for the bladder; Its longer effect (it is not hydrolyzed by cholinesterase) results in prolonged side-effects.

Pyridostigmine may improve tear production by retaining acetylcholine in the synapse, but it does not improve the release of acetylcholine and it increases the risk of systemic side-effects found in cholinergic medications such as dizziness, drowsiness, lightheadedness, headache, nausea, vomiting, abdominal cramps/pain, diarrhea, increased salivation or urination, headache, slow heart rate followed by fast heart rate, and sweating. Additionally, there is evidence that Pyridostigmine can initiate and prolong neurodegeneration by causing apoptosis in the cerebral cortex and that such apoptosis continued up to 30 days after ingestion (in rats).

The inventor recognizes that muscarinic acetylcholine receptor agonists are contraindicated in asthma, coronary insufficiency peptic ulcers, intestinal obstruction hyperthyroidism (parasympathetic action exacerbates the symptoms of these disorders), limiting their use.

Driscoll (U.S. Pat. No. 10,238,673) found a composition comprising a choline compound, a cholinesterase inhibitor, and Acetyl-L-Carnitine in the amounts summarized in the invention are sufficient to stimulate the postganglionic vagus nerve (a nicotinic acetylcholinergic receptor), resulting in normalized organ function, and relief of dry eyes. A limitation of this invention for use in dry eyes is that stimulation of the vagus nerve is a necessary consequence of the compound, but for those patients who suffer with dry eyes and/or dry mouth without vagus nerve dysfunction, this stimulation can cause unnecessary vagal and cholinergic symptoms. Localized inflammation affecting lacrimal nerve function contributes to chronic dry eyes. Such inflammation may not involve vagus nerve functions. If the vagus nerve (or additional parasympathetic systems) is simultaneously stimulated in attempt to stimulate the lacrimal nerve, the excessive systemic parasympathetic nervous system activation can cause side-effects such as salivation, sweating, diarrhea and gastrointestinal distress, emesis, urination, defecation, and muscle spasm.

The current invention eliminates dry eyes without necessarily stimulating the vagus nerve, and without the consequences and limitations of cholinergic prescription medications.

Ingredients. The present invention is a composition that includes 2 or 3 or 4 of the following: (1) Cholinesterase inhibitors (acetylcholinesterase inhibitors); (2) any form of choline; (3) any form of carnitine; and (4) any muscarinic agonist. Optional additions to the present invention include: thiamin, magnesium, and/or alpha-lipoic acid.

Conditions treated. Connective tissue disorders (including those of fibrillin, microfibrillin, elastin, collagen, tenascin-x) can disrupt both the ocular tissue itself (including the tissue of the eyelids) and encourage the inflammatory cascade, resulting in infiltration of inflammatory cells.

Similar inflammatory conditions that are addressed by this patent include aging, disorders of TGF-beta, SMAD, RCCX, CYP21A2, MCP-1, TNX, Fibrillin-1, Fibrillin-3, microfibrillin, mast cell activation disorders, autoimmunity, autoinflammatory conditions, inflammation due to stress, post-viral inflammation (including post-SARS, post-COVID), autoimmunity, Sjogren syndrome, NSDE (Non-Sjogren's Dry Eye), antibodies to muscarinic (M3) receptors, aging.

Diseases or conditions that exhibit with, cause, or worsen dry eyes include: Keratoconjunctivitis sicca, Aqueous deficiency dry eye disease (ADDE), allergies, Sjogren's syndrome, Evaporative Dry Eye (EDE), pterygium, Vitamin A deficiency, blepharitis, meibomian gland disease, allergic conjunctivitis, pterygium, ocular symptoms of graft versus host disease, ocular allergy, atopic keratoconjunctivitis, vernal keratoconjunctivitis, uveitis, anterior uveitis, Bechet's disease, Steven Johnson syndrome, ocular cicatricial pemphigoid, chronic ocular surface inflammation caused by viral infection, herpes simplex keratitis, ocular rosacea, pinguecula, dry eyes associated with refractive surgery (or other ocular surgeries), due to damage to the pre- or post-ganglionic lacrimal nerve, associated with connective tissue disorders, in conjunction with chronic inflammatory conditions such as eosinophilic disorders; Diseases or conditions that are worsened by genetic disorders of inflammation (RCCX, CYP21A2, disorders of the TGF-beta cascade, MCP-1, TNX, SMAD), autoimmune disorders, abnormal hormones (androgens, estrogens or both), mast cell activation disorders, genetic disorders of tryptase, eosinophilic disorders (eosinophilic esophagitis, eosinophilic gastroenteritis, eosinophilia), adrenal disorders, congenital adrenal hyperplasia, Hyper IgE syndrome, low immune system (low $IgG_1$, $IgG_2$, $IgG_3$, $IgG_4$, or IgA), Idiopathic Intracranial Hypertension (IIH), post-infective inflammation (post-viral, post-SARS, post-COVID, or post-bacterial); vascular inflammation, vascular oxidation, hemochromatosis, hemolysis, reduced levels of nitric oxide, or impaired release of acetylcholine, autonomic dysfunction (dysautonomia, Postural Orthostatic Tachycardia Syndrome); acquired disorders of connective tissue as seen in Ehlers-Danlos syndrome, Marfan's syndrome, Loeys-Dietz syndrome, Stickler syndrome, fibrillin disorders, elastin disorders, Joint Hypermobility Syndrome.

Evaporative dry eye (EDE). Can include: tear film instability, hyperosmolarity of tears, characterized by ocular surface inflammation, corneal damage, and neurosensory abnormalities; it may involve increased ocular pain and sensitization, neuropathic pain.

Dry eyes related to sex, gender, hormones, effects of sex steroids, hypothalamic-pituitary hormones, glucocorticoids, insulin, insulin-like growth factor 1, thyroid hormones.

Sex-related dry eyes including differences in parent-of-origin effects, X-chromosome gene dosage (ex: X-inactivation), genes in the non-recombing region of the Y-chromosome, and from sex-specific autosomal factors and epigenetics.

Meibomian gland dysfunction (MGD)-related Dry Eye Disease (MDG-DED)—with tear film lipid layer deficiency. Any DED can have a secondary evaporative element.

DED due to blocking of the sensory drive to the lacrimal gland, due to trauma including, but not limited to LASIX surgery.

Dry eyes worsened with drugs (iatrogenic): antihistamines, beta-blockers, antispasmodics, diuretics, some psychotropic drugs, cis-retinoic acid, polychlorinated biphenyls; skin disorders, acne rosacea, atopic dermatitis, seborrheic dermatitis, psoriasis, cicatricial conjunctival diseases such as trachoma, erythema multiforme and pemphigoid.

This compound treats or prevents dry eyes associated with at least one of immune disorders, autoinflammatory disorders, a rheumatological disease, or Postural Orthostatic Tachycardia Syndrome (POTS).

This compound treats dry eyes related to genetic and/or acquired disorders of connective tissue (which may include Ehlers-Danlos syndrome, Marfan's syndrome, Loeys-Dietz syndrome, Stickler syndrome, fibrillin disorders, elastin disorders, Joint Hypermobility Syndrome) chronic infectious and/or fatigue syndrome including Chronic Fatigue Syndrome, COVID "Longhaulers" or Post-Acute Sequelae of SARS-CoV-2, Myalgic Encephalomyelitis, Post-Traumatic Stress Disorder, mild traumatic brain injury, Chronic Lyme disease, fibromyalgia; autoimmune disorders which may include multiple sclerosis, a vascular disease and a rheumatological disease.

The present invention can be used to treat or prevent dry eyes associated with Postural Orthostatic Tachycardia Syndrome ("POTS"), post-viral and post-infective autonomic dysfunction, chronic dry eyes, visual snow, and idiopathic dysautonomia (disorders of the autonomic nervous system). These chronic conditions possess some commonalities, but treatment based on the underlying medical origination of illness are lacking. Associated conditions include traumatic brain injury (TBI), Post Traumatic Stress Disorder (PTSD)), post-infectious Postural Orthostatic Tachycardia Syndrome, inflammatory autonomic dysfunction and Inflammatory Postural Orthostatic Tachycardia Syndrome, genetic disorders of RCCX, CYP21A2, disorders of the TGF-beta cascade, TNX, SMAD), autoimmune disorders, abnormal hormones (androgens and estrogens), genetic disorders of tryptase (including hereditary alpha tryptasemia), Hyper IgE Syndrome, low immune system (low IgG, low IgA), Idiopathic Intracranial Hypertension (IIH), vascular oxidation (including that due to hemochromatosis and hemolysis), low nitric oxide, impaired release of acetylcholine, genetic disorders of the acetylcholine manufacturing cycle. The present invention is uniquely designed to simultaneously correct or control the underlying causes and associated conditions related to dry eyes sufficiently to arrest the progression of illness resulting in this vast array of symptoms and signs.

Dry eyes diagnostic methodology. Traditionally, the sequela of the inflammation involved in chronic dry eyes is what is measured, not the primary condition. Testing includes (but is not limited to):

Tear break up time, corneal staining (fluorescein and rose bengal), imaging of the meibomian glands, measurements of MMP-9, measurements of lactoferrin, tear osmolality, corneal topography, visual acuity, Sjogren's Syndrome testing (Sjo blood tests, blood tests for autoimmunity), corneal topography, Schirmer testing, Phenol Red Thread, and evaluation of symptoms.

Conjunctival impression cytology is a relatively non-invasive technique for ocular (bulbar) conjunctival biopsy for specimen collection in cases of suspected ocular surface squamous neoplasia. It has also been used to diagnose and monitor acanthamoeba keratitis, Steven-Johnson's syndrome, trachoma, alkali burns, keratoconjunctivitis sicca, and xerophthalmia by interpreting the nucleus:cytoplasm ratio of epithelial cells of the ocular conjunctiva. As dry eyes worsen, the ratio of nucleus:cytoplasm of the epithelial cells decreases. This technique measures the level of dryness but not the amount or type of inflammatory cells present. Some researchers are using this technique to test specific markers of inflammation, cytokines, and chemokines. This technique has not been widely accepted for routine dry eye evaluation because it is cumbersome and requires a pathologist, ophthalmologist, and immunologist for proper interpretation, and it adds no new information for the dry eye patient with no evidence of neoplasia, Steven-Johnson's syndrome, trachoma, or burns. Current conjunctival impression cytology testing is limited because a positive test result (abnormal nucleus:cytoplasm ratio of the epithelial cells) reflects dryness, but not necessarily inflammation.

Conjunctival cytology for testing patients with chronic dry eyes.

In this unique technique, the sample is examined for inflammatory cells (not examined for the nucleus:cytoplasm ratio of the epithelial cells of the conjunctiva). The sample is not taken from the bulbar or ocular conjunctiva, but is instead retrieved from the palpebral conjunctiva (a more robust tissue less likely to result in redness of the ocular conjunctiva that can cause patient distress, located further from the delicate cornea—minimizing the possibility of corneal injury during sample retrieval, and located closer to the lacrimal gland, the meibomian glands, and the accessory glands, thereby reflecting a more accurate inflammatory assessment of the environment for the lacrimal nerve and receptors of the lacrimal gland). Palpebral conjunctival samples are evaluated for inflammatory cells that may contribute to chronic dry eyes, and to confirm suspected interference with the release of the neurotransmitter utilized by the lacrimal nerve (part of the parasympathetic nervous system). If lymphocytes or neutrophils are (neurologically) contributing to poor lacrimal nerve function, as can occur in early Sjogren's, the muscarinic receptors on acinar cells of the lacrimal gland and accessory glands (the lacrimal gland and accessory lacrimal glands are both treated by the present invention) offer unique targets to stimulate tear production, without vagus nerve stimulation, and respond to treatment with the compositions of the present invention. Biopsy of the lacrimal gland will not reflect this neurological presentation secondary to inflammation until the inflammatory cells invade the gland itself. Instead of utilizing gland involvement for early detection, this method relies on identifying the inflammatory environment that renders the lacrimal nerve insufficient—an earlier presentation.

Conjunctival smears are obtained by first anesthetizing the eye with alcaine 0.5% (or a similar agent), the upper lid is everted (or the lower lid can be used, with care not to scrape the ocular conjunctiva), and a sample is obtained via Kimura spatula or a sanitary "Q-tip" swab moistened with non-preserved saline.

The sample is then transferred to a microscope slide by rolling or tapping the spatula or by rolling the swab on the slide. The slide is then allowed to air dry (no heat) and stained with "Diff-Quick" stain or similar (such as Hemacolor or Wright or Giemsa stain).

Microscopic examination of the slide is performed to examine and identify the types of cells present.

Normal, healthy conjunctival tissue contains epithelial cells, goblet cells, and a rare neutrophil or lymphocyte. If no epithelial cells are found, the specimen is likely insufficient and must be redone.

Conjunctival Study.

A cytology study of 26 patients with chronic dry eyes and symptoms of autonomic dysfunction (such as constipation, tachycardia upon standing—postural orthostatic tachycardia syndrome—POTS and fatigue) was conducted as described. The cytology studies revealed an abnormal number of neutrophils and lymphocytes in the majority of patients. The patient samples appeared similar to those of patients with bacterial or viral infections (yet, without infection). Interestingly, high numbers of lymphocytes were seen even when the epithelial cells appeared normal (the nucleus:cytoplasm ratio was normal) in affected patients.

Then, the inventor analyzed 20 patients with chronic dry eyes (these patients were not questioned about autonomic symptoms such as constipation, tachycardia upon standing or POTS, constipation, or fatigue) and also found the majority of specimens revealed abnormal levels of lymphocytes (including neutrophils).

Next, Ocular Surface Disease Index (OSDI®) scores were obtained for 14 patients with chronic dry eyes who were not questioned about autonomic symptoms beyond dry eyes. OSDI scores before and after treatment were collected and analyzed (Table 2). Patients were treated with Alpha GPC (200 mg), Acetyl-L-Carnitine (75 mg), Huperzine A (75 mcg). Patients reported a significant reduction in the symptoms of dry eyes (as analyzed by the OSDI® score).

Cytology evaluation was a good diagnostic tool to locate the abnormal presence of inflammatory cells and to confirm the interference of neurotransmitter release, but it was not found to be a good quantitative measure of response to treatment. The OSDI® scores, however, were a good quantitative measure of response.

TABLE 2

| Patient # | Neutrophils (grade 0-4) | Lymphocytes (grade 0-4) | OSDI® score- before treatment | OSDI® score- after treatment |
|---|---|---|---|---|
| 1 | 0 | 3 | 29.16 | 6.81 |
| 2 | 0 | 2 | 27.5 | 7.5 |
| 3 | 3 | 0 | 37.5 | 34.1 |
| 4 | 3 | 3 | 41.6 | 13.9 |
| 5 | 3 | 3 | 27.08 | 50 |
| 6 | 0 | 3 | 62.5 | 29.16 |
| 7 | 2 | 2 | 43.75 | 27.1 |
| 8 | 3 | 2 | 55 | 18.18 |
| 9 | 2 | 2 | 31.82 | 13.64 |
| 10 | 3 | 1 | 5.56 | 0 |
| 11 | 4 | 2 | 60.41 | 61.36 |
| 12 | 4 | 1 | 62.5 | 30 |
| 13 | 2 | 4 | 50 | 22.5 |
| 14 | 3 | 3 | 61.36 | 37.5 |

Based on the results above, the inventor conducted the next study, which was a treatment study to look at response to both OSDI® score and Tear Break Up Time (TBUT) and corneal staining for dry eye patients without regard to autonomic symptoms beyond dry eyes.

Figure 2:
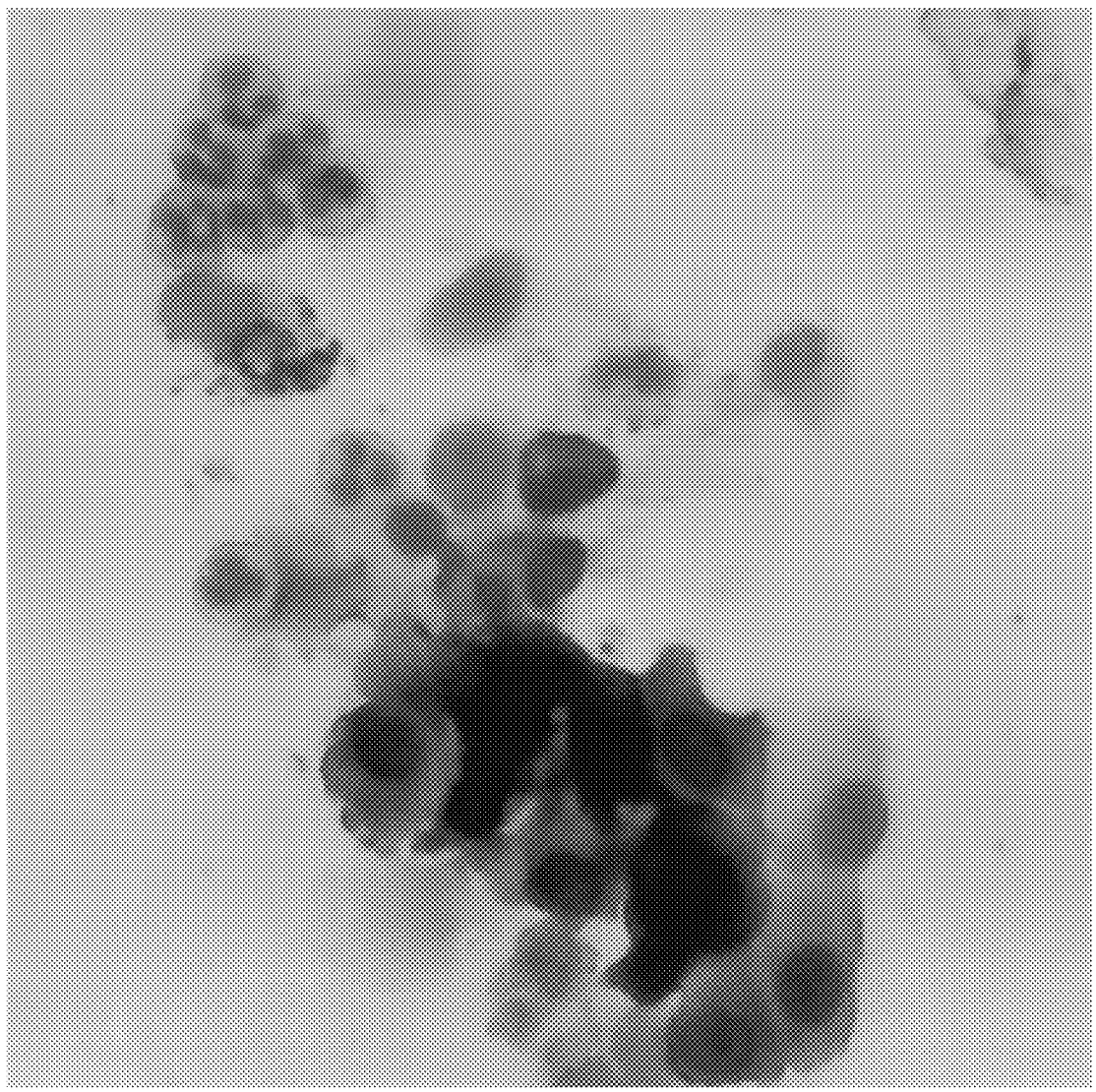
FIG. 2 shows neutrophils obtained from chronic dry eye patient 12, Table 3.

Variations to the compound are summarized below. These results show that it is not always necessary to stimulate the nicotinic vagus nerve to get the dry eye reversal, thereby it was possible to use two or more components, while still preventing or treating the dry eyes. FIG. 1 shows neutrophils obtained from chronic dry eye patient 11. FIG. 2 shows neutrophils obtained from chronic dry eye patient 12.

TABLE 3

Treatment results:

| Patient ID | Treatment (T) or Placebo (P) | Status | Initial TBUT | Final TBUT | Initial corneal staining | Final corneal staining | Initial OSDI score | Final OSDI score |
|---|---|---|---|---|---|---|---|---|
| 1 - RM86 | T | | 4.5 | 9.10 | 2.1 | 0.0 | 45.88 | 27.08 |
| 2 - KM54 | T | | 6.7 | 10.10 | 2.2 | 0.0 | 56.25 | 75 |
| 3 - SM58 | T | | 3.3 | 2.2 | 3.3 | 1.2 | 63.64 | 35.42 |
| 4 - LB81 | T | | 7.5 | 4.4 | 2.1 | 0.0 | 43.75 | 37.5 |
| 5 - FR82 | T | | 5.4 | 8.6 | 4.3 | 3.2 | 41.6 | 26.7 |
| 6 - MM57 | T | | 2.2 | 2.2 | 2.3 | 2.3 | 64.58 | 16.67 |
| 7 - MV54 | T | | 3.4 | 7.8 | 1.2 | 0.0 | 70.83 | 39.58 |
| 8 - GZ43 | T | | 2.2 | 4.5 | 2.2 | 0.1 | 62.5 | 41.67 |
| 9 - KM80 | T | | 2.3 | 6.7 | 3.3 | 1.0 | 70.83 | 14.58 |
| 10 - JJ58 | T | | 5.5 | 6.5 | 1.1 | 1.2 | 58.33 | 60.42 |
| 11 - NE56 | T | | 4.6 | 6.6 | 2.3 | 0.0 | 77.08 | 64.58 |

TABLE 3-continued

Treatment results:

| Patient ID | Treatment (T) or Placebo (P) | Status | Initial TBUT | Final TBUT | Initial corneal staining | Final corneal staining | Initial OSDI score | Final OSDI score |
|---|---|---|---|---|---|---|---|---|
| 12 - AS57 | T | | 5.4 | 6.6 | 3.3 | 2.3 | 75 | 50 |
| KW71 | P | drop out | 2.2 | | 2.3 | | 62.5 | |
| DH58 | P | | 4.4 | 4.4 | 2.2 | 1.3 | 59.1 | 54.54 |
| MM40 | P | | 4.4 | 5.4 | 2.2 | 1.2 | 45.83 | 54.17 |
| JR50 | P | | 2.4 | 3.3 | 3.3 | 2.3 | 77.08 | 83.33 |
| LB81 | P | | 3.5 | 3.4 | 1.1 | 1.2 | 52.08 | 45.83 |
| RB61 | P | | 4.4 | 5.5 | 2.2 | 2.2 | 70.83 | 58.33 |

Compounds given:

1-4: 100 mcg Huperzine A, 400 mg Alpha GPC, 30 mg thiamin 5-8: 700 mg Choline, 300 mg Acetyl-L-Carnitine, 300 mg magnesium citrate 9-12: 150 mg Huperzine A, 150 mg Acetyl-L-Carnitine Placebo: A capsule, same size, same color, filled with baking soda and corn starch.

The compounds resulted in no side-effects and no bowel movement reflecting vagus nerve stimulation.

Treatment group:

Improved corneal staining: 92%
Improved OSDI score: 83%
Improved TBUT: 75%

Placebo group:

Improved corneal staining: 60%
Improved OSDI score: 40%
Improved TBUT: 60%

Case Study 1:

Female, 54 with chronic dry eyes unresponsive to numerous treatments (moisture drops, cellulose discs, punctal plugs, warm compresses with massage, ointment at night, Restasis). She was forced to discontinue her contact lenses and use eye drops numerous times a day.

Corneal staining minimal (grade 2 inferiorly), and TBUT (tear break up time) was 2 seconds. Grade 2 conjunctival injection. Cytology (conjunctival smears with diff-quick stain) revealed some monocytes and numerous neutrophils. The patient did not have any signs of ocular infection or ocular allergy. The patient reported no itching. OSDI: 62.5

Using an antioxidant blend of 400 mg NAC, 400 mg tumeric, 50 mg alpha-lipoic acid, 50 mg Vitamin C, she experienced a very slight improvement in OSDI (59.1).

This antioxidant blend was discontinued, and she began taking 600 mg choline with 300 mg Acetyl-L-Carnitine. In 4 weeks, her OSDI® score improved to 45.5.

Then she combined the choline and Acetyl-L-Carnitine with the antioxidant blend.

Within 4 weeks of use, her dry eyes were significantly improved, and she was able to wear her contact lenses again comfortably without eye drops. OSDI:10.4. Interestingly, by report, her overall wellness was also dramatically improved—cognition, fatigue, bowel movements had all improved.

| Pretreatment OSDI | POST Tx Antioxidant Blend – OSDI | Post Tx Choline + Acetyl-L-Carnitine – OSDI | Post Tx Choline + Acetyl-L-Carnitine + Antioxidant Blend |
|---|---|---|---|
| 62.5 | 59.1 | 45.5 | 10.4 |

Case Study 2.

Male, 14 years old, suffered from non-allergic dry eyes. His blink became abnormal (he rolled his eyes around when he blinked) in an attempt to distribute moisture in his eyes. His eyes exhibited no corneal staining, but also no tear meniscus. The patient did not experience itching. TBUT (tear break up time) was 3 seconds. Eye drops were ineffective. Cytology revealed lymphocytes and neutrophils.

Within 3 weeks of supplementation with antioxidant blend (200 mg N-acetylcysteine, 5 mcg selenium, 250 mg curcumin), his dry eyes improved from an OSDI® score of 68.2 to 65.9. He then discontinued the antioxidant blend and began taking 100 mcg Huperzine A, 400 mg Alpha GPC, 30 mg thiamin. His dry eyes improved (OSDI® score of 40). When the antioxidant blend was combined with the same doses of Huperzine A, Alpha GPC, and thiamin, his dry eyes completely resolved. OSDI® score pre-treatment: 68.2 post-treatment: 13.63.

| Pretreatment OSDI | Post Tx Antioxidant Blend – OSDI | Post Tx Huperzine A + Alpha GPC + Thiamin – OSDI | Post Tx Huperzine A + Alpha GPC + Thiamin + Antioxidant Blend |
|---|---|---|---|
| 68.2 | 65.9 | 40 | 13.63 |

The present invention also includes treating some signs and symptoms of dry eye that may not be just due to dry corneas, but instead due to large pupils because of faulty neurology—poor acetylcholine release that also contributes to low tear production.

Thus, the present invention can also be used to diagnose and treat neurological dry eye using the compound and measuring pupil size before and after administration of the compositions taught herein.

It was found that the same type of receptors (muscarinic parasympathetic receptors) make the pupils smaller and promote tear production (both the lacrimal gland and the meibomian glands). By measuring the pupil response to treatment (a test for neurological dry eye), it is possible to properly diagnose neurological dry eye and treat it effectively with the present invention. The test for neurological dry eye can be used to measure the effectiveness of the composition and the treatment, thus, the present invention uses an objective measure of the underlying neurology to test for the effectiveness of the treatment.

The activity of the muscarinic receptors serving the lacrimal glands are measured by the change in pupil size with the compound. As shown herein, dry eye is associated with an increase in average pupil size, as such, the effectiveness of the treatment is found when the patient's pupils get smaller. As shown in Table 3, it was possible not only detect the presence of dry eye by measuring pupil size, it was also possible to show the effectiveness of the composition for treating the dry eye. It was found that in these patients the large pupils normalize in 12-36 hours after treatment.

Further, chronic dry eye patients suffer from light sensitivity and some visual problems such as difficulty focusing, difficulty reading up close, and variable vision. The skilled artisan generally presumes that this is due to desiccation of the cornea. However, it was found herein that, clinically, this is not what patients usually demonstrate. The majority of chronic dry eye patients suffer with much more light sensitivity and visual disturbance than what is warranted by their corneal desiccation, as determined by a corneal staining score.

Measure pupil size by traditional means (using an autorefractor) with controlled lighting that is repeatable, administer the compound, measure pupil size in the same manner at 12, 24, 36, 48, 72, 96, 120 hours. Smaller pupil size reflects viable muscarinic receptors and is diagnostic of neurological dry eye. If lacrimal glands are viable, patients will respond with increased (aqueous) tear production. If meibomian glands are viable and not structurally damaged or clogged, patients will respond with increased meibomian gland release of the oily layer of tears. Light sensitivity and visual disturbances will also improve.

TABLE 3

| Patient # | Initial Pupil Size mm (autorefractor) | Final Pupil Size mm |
|---|---|---|
| 1 | 6 | 4.5 |
| 2 | 5 | 4 |
| 3 | 6.5 | 6.0 |
| 4 | 7 | 5.5 |
| 5 | 8 | 6.5 |
| 6 | 5.5 | 4.5 |
| 7 | 5.5 | 4 |
| 8 | 6 | 4 |
| 9 | 6.5 | 4.5 |
| 10 | 5.5 | 4.5 |
| 11 | 6 | 5 |
| 12 | 8 | 6 |
| Placebos: | | |
| 1 | 4 | 4 |
| 2 | 4.5 | 4 |
| 3 | 4 | 4.5 |
| 4 | 3.5 | 4 |
| 5 | 5 | 5 |
| 6 | 4.5 | 4.5 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Dartt D A. Neural regulation of lacrimal gland secretory processes: relevance in dry eye diseases. Prog Retin Eye Res. 2009; 28(3):155-177. doi:10.1016/j.preteyeres.2009.04.003

Hocevar, A, T. M. (2003). Parasympathetic nervous system dysfunction in primary Sjogren's Syndrome. Ann Rheum Dis, 702-704.

Li L, J. D. (2012). Activities of autonomic neurotransmitters in Meibomian gland tissues are associated with menopausal dry eyes. Neural Regen Res, 2761-2769.

Vincent A, M. S. (2014). A report of the autonomic symptom profile in patients with fibromyaliga. J Clin Rheumatol, 106-108.

Proctor G B, Carpenter G H. Regulation of salivary gland function by autonomic nerves. Auton Neurosci. 2007 Apr. 30; 133(1):3-18. doi: 10.1016/j.autneu.2006.10.006. Epub 2006 Dec. 6. PMID: 17157080.

Li L, Gunasekar P G, Borowitz J L, Isom G E. Muscarinic receptor-mediated pyridostigmine-induced neuronal apoptosis. Neurotoxicology. 2000 August; 21(4):541-52. PMID: 11022862.

LeDoux M S, Zhou Q, Murphy R B, Greene M L, Ryan P. Parasympathetic innervation of the meibomian glands in rats. Invest Ophthalmol Vis Sci. 2001 October; 42(11): 2434-41. PMID: 11581180.

Craig J P, Nelson J D, Azar D T, Belmonte C, Bron A J, Chauhan S K, de Paiva C S, Gomes J A P, Hammitt K M, Jones L, Nichols J J, Nichols K K, Novack G D, Stapleton F J, Willcox M D P, Wolffsohn J S, Sullivan D A. TFOS DEWS II Report Executive Summary. Ocul Surf 2017 October; 15(4):802-812. doi: 10.1016/j.jtos.2017.08.003. Epub 2017 Aug. 8. PMID: 28797892.

Zoukhri D, Kublin C L. Impaired neurotransmitter release from lacrimal and salivary gland nerves of a murine model of Sjögren's syndrome. Invest Ophthalmol Vis Sci. 2001 April; 42(5):925-32. PMID: 11274068; PMCID: PMC3241007.

Passafaro D, Sterin-Borda L, Reina S, Borda E. Cholinergic Autoantibodies from Primary Sjögren's Syndrome Inhibit Mucin Production via Phospholipase C and Cyclooxygenase-2 In the Rat Submandibular Gland. Dent Res J (Isfahan). 2011; 8(3):138-145.

Conrady C D, Joos Z P, Patel B C. Review: The Lacrimal Gland and Its Role in Dry Eye. J Ophthalmol. 2016; 2016:7542929. doi:10.1155/2016/7542929

Mahboob A, Farhat S M, Iqbal G, Babar M M, Zaidi N U, Nabavi S M, Ahmed T. Alpha-lipoic acid-mediated activation of muscarinic receptors improves hippocampus- and amygdala-dependent memory. Brain Res Bull. 2016 April; 122:19-28. doi: 10.1016/j.brainresbull.2016.02.014. Epub 2016 Feb. 18. PMID: 26912408.

Tsuboi H, Matsumoto I, Wakamatsu E, et al. New epitopes and function of anti-M3 muscarinic acetylcholine receptor antibodies in patients with Sjögren's syndrome. Clin Exp Immunol. 2010; 162(1):53-61. doi:10.1111/j.1365-2249.2010.04188.x Singh R, Joseph A, Umapathy T, Tint N L, Dua H S. Impression cytology of the ocular surface. Br J Ophthalmol. 2005; 89(12):1655-1659. doi:10.1136/bjo.2005.073916

Reddy M, Reddy P R, Reddy S C. Conjunctival impression cytology in dry eye states. Indian J Ophthalmol. 1991 January-March; 39(1):22-4. PMID: 1894340.

Hagan H. Biomarkers of ocular surface disease using impression cytology. Biomarkers in Medicine. 2017 11:12, 1135-1147

Ozcura F, Aydin S, Helvaci M R. Ocular surface disease index for the diagnosis of dry eye syndrome. Ocul Immunol Inflamm. 2007 September-October; 15(5):389-93. doi: 10.1080/09273940701486803. PMID: 17972223.

Mitchelson F. Muscarinic receptor agonists and antagonists: effects on ocular function. Handb Exp Pharmacol. 2012; (208):263-298. doi:10.1007/978-3-642-23274-9_12

What is claimed is:

1. A method for using conjunctival cytology of a patient suspected to detect neurologic chronic dry eye prior to damage to a lacrimal gland, comprising:

obtaining a sample from the palpebral conjunctiva;
staining the sample to detect inflammatory cells; and
determining that the patient has neurologic dry eyes due to the presence of inflammatory cells near the lacrimal nerve, wherein epithelial cells in the palpebral conjunctiva have a normal nucleus to cytoplasm ratio, and wherein the inflammatory cells cause a lacrimal nerve insufficiency that causes the chronic dry eyes.

2. The method of claim 1, wherein the sample is examined for an increase in inflammatory cells in the conjunctiva.

3. The method of claim 1, wherein if the patient has the lacrimal nerve insufficiency or dry eye, administering to the patient a composition comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes.

4. The method of claim 1, wherein the composition further comprises:
at least one of 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg;
at least one of an antioxidant, magnesium thiamin, or alpha lipoic acid, and if magnesium is provided it is selected from at least one of magnesium glycinate, magnesium oxide, magnesium chloride, magnesium lactate, magnesium carbonate, magnesium citrate, and/or magnesium threonate and is provided at between 0.1, 0.5, 1, 5, 10, 20, 30, 40, 50, 60, 70, 80, 90, 100, 150, 200, 250, 270, 300, 350, 400, 450, 500, 600, 700, 750, 800 mgs elemental magnesium; or if thiamin (thiamin/Vitamin B1) is provided at between 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600 mg, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg; or
at least one of an antioxidant selected from Vitamin C at 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg; Vitamin E at 1, 5, 10, 20, 30, 40, 50, 60, 70, 80, 90, 100, 150, 200, 250, 270, 300, 350, 400, 450, 500, 540, 600, 700, 750, 800 mg; N-acetylcysteine at 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg; Selenium at 0.1, 0.2, 0.3, 0.5, 0.75, 1, 5, 10, 20, 30, 40, 50, 60, 70, 80, 90, 100, 150, 200, 250, 270, 300, 350, 400 mcg; and Curcumin at 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg.

5. A method for treating at least one of chronic dry eye prior to damage to a lacrimal gland, neurological dry eye, or dry corneas, comprising:
obtaining a sample from the palpebral conjunctiva of a patient;
staining the sample to detect inflammatory cells; and
determining that the patient has neurologic dry eyes due to the presence of inflammatory cells near the lacrimal nerve, wherein epithelial cells in the palpebral conjunctiva have a normal nucleus to cytoplasm ratio, and wherein the inflammatory cells cause a lacrimal nerve insufficiency that causes the chronic dry eyes;
wherein if the patient has lacrimal nerve insufficiency, administering to the patient a composition comprising an effective amount of at least two active agents selected from: (1) at least one cholinesterase inhibitor; (2) at least one form of choline; (3) at least one form of carnitine; or (4) at least one form of muscarinic agonist, sufficient to treat the disease or condition that causes dry eyes.

6. The method of claim 5, wherein the sample is examined for an increase in inflammatory cells in the conjunctiva; or measuring pupil size before and after administration of the composition, wherein above-average pupil size that becomes smaller with treatment of the compound is diagnostic of neurological dry eye; wherein the symptoms and signs of dry eyes and low tear production by either acinar cells of the lacrimal gland or cells of meibomian glands as determined by at least one of: tear film instability, hyperosmolarity of tears, ocular surface inflammation, corneal damage, neurosensory abnormalities; increased ocular pain and sensitization, neuropathic pain, light sensitivity, decreased accommodation, fluctuating vision, pupils that are larger than average.

7. The method of claim 5, wherein if the patient has the lacrimal nerve insufficiency, treating the patient with a composition comprising at least two active agents selected from: (1) at least one cholinesterase inhibitor; (2) at least one form of choline; (3) at least one form of carnitine; (4) at least one form of muscarinic agonist, sufficient to treat the disease or condition that causes dry eyes; wherein the composition activates muscarinic receptors on acinar cells of a lacrimal gland, accessory lacrimal glands, or both to stimulate tear production without vagus nerve stimulation.

8. The method of claim 5, wherein the composition further comprises:
at least one of 0.1, 0.5, 1, 5, 10, 20, 30, 40, 50, 60, 70, 80, 90, 100, 150, 200, 250, 300, 350, 400, 450, 500, 550, 600 mg thiamin, and the dose is 0.1, 0.2, 0.3, 0.5, 0.75, 1.0, 5, 10, 15, 20, 25, 30, 40, 50, 60, 70, 80, 90, 100, 150, 200, 250, 300, 350, 400, 450, 500, 540, 600, 700, 750, 800 mg Magnesium, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg;
at least one of an antioxidant, magnesium, thiamin, or alpha lipoic acid, and if magnesium is provided it is selected from at least one of magnesium glycinate, magnesium oxide, magnesium chloride, magnesium lactate, magnesium carbonate, magnesium citrate, or magnesium threonate and is provided at between 0.1, 0.5, 1, 5, 10, 20, 30, 40, 50, 60, 70, 80, 90, 100, 150, 200, 250, 270, 300, 350, 400, 450, 500, 600, 700, 750, 800 mgs elemental magnesium;

or if thiamin (thiamin/Vitamin B1) is provided at between 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600 mg, or alpha-lipoic acid is 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg; at least one of an antioxidant selected from Vitamin C at 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg; Vitamin E at 1, 5, 10, 20, 30, 40, 50, 60, 70, 80, 90, 100, 150, 200, 250, 270, 300, 350, 400, 450, 500, 540, 600, 700, 750, 800 mg; N-acetylcysteine at 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000 mg; Selenium at 0.1, 0.2, 0.3, 0.5, 0.75, 1, 5, 10, 20, 30, 40, 50, 60, 70, 80, 90, 100, 150, 200, 250, 270, 300, 350, 400 mcg; and Curcumin at 0.1, 0.2, 0.3, 0.5, 0.75, 1, 5, 10, 20, 30, 40, 50, 60, 70, 80, 90, 100, 150, 200, 250, 270, 300, 350, 400, 450, 500, 540, 600, 700, 750, 800, 900, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000 mg.

9. The method of claim 5, wherein the composition stimulates at least one of: muscarinic receptors of ocular pupils, lacrimal gland, or meibomian glands.

* * * * *